United States Patent
Alsan et al.

(10) Patent No.: US 11,113,813 B2
(45) Date of Patent: Sep. 7, 2021

(54) EVALUATING A CONDITION OF A PERSON

(71) Applicant: Siemens Healthcare GmbH, Erlangen (DE)

(72) Inventors: Alper Alsan, Erlangen (DE); Elif Kirmizi-Alsan, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 71 days.

(21) Appl. No.: 16/597,266

(22) Filed: Oct. 9, 2019

(65) Prior Publication Data
US 2020/0118269 A1 Apr. 16, 2020

(30) Foreign Application Priority Data

Oct. 15, 2018 (EP) .................... 18200394

(51) Int. Cl.
*G06K 9/00* (2006.01)
*G06T 7/00* (2017.01)
*A61B 5/00* (2006.01)

(52) U.S. Cl.
CPC .......... *G06T 7/0016* (2013.01); *A61B 5/4082* (2013.01); *A61B 5/7267* (2013.01); *G06K 9/00315* (2013.01); *G06T 2207/10016* (2013.01); *G06T 2207/20081* (2013.01); *G06T 2207/30004* (2013.01); *G06T 2207/30201* (2013.01)

(58) Field of Classification Search
CPC .................................................. G06T 7/0016
See application file for complete search history.

(56) References Cited

U.S. PATENT DOCUMENTS

| 2012/0121133 | A1* | 5/2012 | Park | G06T 7/254 |
| | | | | 382/103 |
| 2017/0185827 | A1* | 6/2017 | Yamaya | G10L 25/78 |
| 2019/0246921 | A1* | 8/2019 | Wu | A61B 5/024 |

(Continued)

OTHER PUBLICATIONS

Bandini, Andrea et al.: "Analysis of facial expressions in parkinson's disease through video-based automatic methods"; in: Journal of Neuroscience Methods; vol. 281; pp. 7-20; 2017; DOI: 10.1016/j.jneumeth.2017.02.006.

(Continued)

*Primary Examiner* — Oneal R Mistry
(74) *Attorney, Agent, or Firm* — Harness, Dickey & Pierce, P.L.C.

(57) ABSTRACT

A computer-implemented method is for evaluating a condition of a person. The method includes determining at least one characteristic of a first facial expression of at least a mouth of the person, at a first time, based at least on a first image previously captured; determining at least one characteristic of a second facial expression of at least a mouth of a person, at a second time, based at least on a second image previously captured, the first facial expression and the second facial expression being of a same first type of facial expression; determining at least one difference between the at least one characteristic of the first facial expression determined and the at least one characteristic of the second facial expression determined; and generating an output signal indicating the condition of the person based at least on the at least one difference determined.

23 Claims, 3 Drawing Sheets

(56) References Cited

U.S. PATENT DOCUMENTS

2020/0126283 A1\* 4/2020 van Vuuren ............ G10L 13/00
2020/0401215 A1\* 12/2020 Moffat ................. G06K 9/0061

OTHER PUBLICATIONS

Livingstone, Steven R. et al.: "Deficits in the Mimicry of Facial Expressions in Parkinson's Disease"; in: Frontiers in Psychology; vol. 7; No. 780; 2016; DOI: 10.3389/fpsyg.2016.00780.
Perlmutter, Joel S. et al.: "Assessment of Parkinson Disease Manifestations"; in: Current protocols in Neuroscience; Chapter 10; Unit 10.1; 2009; doi: 10.1002/0471142301.ns1001s49.
Fereshtehnejad, Seyed-Mohammad et al.: "Evolution of Orofacial Symptoms and Disease Progression in Idiopathic Parkinson's Disease: Longitudinal Data from the Jönköping Parkinson Registry"; in: Parkinson's Disease; vol. 2017;Article ID 7802819; 2017; DOI: 10.1155/2017/7802819.
Ricciardi, Lucia et al.: "Rehabilitation of hypomimia in Parkinson's disease: a feasibility study of two different approaches"; in: Neurological Sciences; vol. 37; No. 3; pp. 431-436; 2016; doi: 10.1007/s10072-015-2421-9.
Extended European Search Report for European Application No. 18200394.7 dated Mar. 27, 2019.

\* cited by examiner

US 11,113,813 B2

EVALUATING A CONDITION OF A PERSON

PRIORITY STATEMENT

The present application hereby claims priority under 35 U.S.C. § 119 to European patent application number EP 18200394.7 filed Oct. 15, 2018, the entire contents of which are hereby incorporated herein by reference.

FIELD

Embodiments of the invention generally relates to a system and a computer-implemented method for evaluating a condition of a person, in particular for evaluating a condition of a person with respect to Parkinson's Disease. However, embodiments of the present method may also be used to determine a condition of a person with respect to the mood of the person or with respect to a state of attention of the person.

BACKGROUND

Parkinson's Disease is a long-term degenerative disorder of the central nervous system that mainly affects the motor system. At present, there is no cure for Parkinson's Disease, but a variety of medications provide relief from the symptoms. There are also attempts to stem the progression of the disease as soon as it has been diagnosed, for example by having a patient train using a specially-designed training apparatus.

For all attempts at alleviating the disease it is helpful if the disease is discovered as soon as possible. It is known that facial expressions of the patient can provide information to a physician about whether the patient is suffering from Parkinson's Disease or from another type of nervous disorder.

In particular the posed smiling and voluntary grinning of patients with Parkinson's Disease are abnormal as such patients present profoundly weakened and/or delayed smiles.

For example, the scientific publication by Bandini et al., "Analysis of facial expressions in parkinson's disease through video-based automatic methods", Journal of Neuroscience Methods 281 (2017) 7-20, describes the study of facial bradykinesia in Parkinson's disease. Facial bradykinesia consists in the reduction/loss of facial movements and emotional facial expressions called hypomimia. A video-based approach is proposed.

Further scientific publications in this field are, for example:
Ricciardi et al., "Rehabilitation of hypomimia in Parkinson's disease: a feasibility study of two different approaches", Neurological Sciences March 2016, Volume 37, Issue 3, pp. 431-436.
Fereshtehnejad et al., "Evolution of Orofacial Symptoms and Disease Progression in Idiopathic Parkinson's Disease: Longitudinal Data from Jönköping Parkinson Registry", Parkinsons Dis. 2017, 2017:7802819, doi:10.1155/2017/7802819.
Livinstone et al., "Deficits in the Mimicry of Facial Expressions in Parkinson's Disease", Front Psychol. 2016 Jun. 7, 7:780, doi:10.3389/fpsyg.2016.00780.
Perlmutter, "Assessment of Parkinson Disease Manifestations", Curr. Protoc. Neurosci., 2009 October, Chapter: Unit10.1., doi:10.1002/0471142301.ns1001s49.

SUMMARY

The inventors have discovered that it is cumbersome and inconvenient for a patient to visit a skilled physician with recommended regularity in order to detect the onset of Parkinson's Disease as soon as possible. On the other hand, the inventors have discovered that the patients themselves are usually not skilled enough to diagnose the tell-tale signs in their own facial expressions with sufficient accuracy.

At least one embodiment of the present invention provides a computer-implemented method for evaluating a person's condition, in particular for evaluating a person's condition with respect to Parkinson's Disease.

According to a first embodiment, the present invention provides a computer-implemented method for evaluating a condition of a person, comprising:
acquiring a first image of at least a mouth of a person at a first time at which the person is performing a first facial expression;
determining at least one characteristic of the first facial expression based at least on the acquired first image;
acquiring a second image of at least the mouth of the person at a second time at which the person is performing a second facial expression,
wherein the first facial expression and the second facial expression are of the same first type of facial expression;
determining the at least one characteristic of the second facial expression based at least on the acquired second image;
determining at least one difference between the determined at least one characteristic of the first facial expression and the determined at least one characteristic of the second facial expression; and
generating an output signal indicating the condition of the person based at least on the at least one determined difference.

According to a second embodiment, the present invention provides a system for evaluating a patient's condition, the system comprising:
an image capturing device configured to:
acquire a first image of at least a mouth of a person at a first time at which the person is performing a first facial expression and
acquire a second image of at least the mouth of the person at a second time at which the person is performing a second facial expression wherein the first facial expression and the second facial expression are of the first type of facial expression, in particular a smiling facial expression; and
a computing device configured to:
determine, based at least on the acquired first image, at least one characteristic of the first facial expression;
determine, based on at least the acquired second image, the at least one characteristic of the second facial expression;
determine a difference between the determined at least one characteristic of the first facial expression and the determined at least one characteristic of the second facial expression; and
generate an output signal indicating the condition of the person based at least on the determined difference.

According to a third embodiment, the invention provides a non-transitory computer-readable data storage medium comprising executable program code configured to, when executed, perform the method according to an embodiment of the first embodiment.

According to a fourth embodiment, the invention provides a computer program product comprising executable program code configured to, when executed, perform the method according to an embodiment of the first embodiment.

According to a fifth embodiment, the invention provides a data stream representing, or configured to provide, program code configured to, when executed, perform the method according to an embodiment of the first embodiment.

According to another embodiment, the invention provides a computer-implemented method for evaluating a condition of a person, comprising:

acquiring a first image of at least a mouth of a person at a first time at which the person performs a first facial expression;

determining at least one characteristic of the first facial expression based at least on the first image acquired;

acquiring a second image of at least the mouth of the person at a second time at which the person performs a second facial expression, the first facial expression and the second facial expression being of a same first type of facial expression;

determining at least one characteristic of the second facial expression based at least on the second image acquired;

determining at least one difference between the at least one characteristic of the first facial expression determined and the at least one characteristic of the second facial expression determined; and generating an output signal indicating the condition of the person based at least on the at least one difference determined.

According to another embodiment, the invention provides a system for evaluating a condition of a person, comprising:
   an image capturing device configured to:
   acquire a first image of at least a mouth of the person at a first time at which the person performs a first facial expression, and
   acquire a second image of at least the mouth of the person at a second time at which the person performs a second facial expression, the first facial expression and the second facial expression being of a same first type of facial expression; and
   a computing device configured to:
   determine, based at least on the first image acquired, at least one characteristic of the first facial expression;
   determine, based on at least the second image acquired, the at least one characteristic of the second facial expression;
   determine a difference between the at least one characteristic of the first facial expression determined and the at least one characteristic of the second facial expression determined; and
   generate an output signal, indicating the condition of the person based at least on the difference determined.

According to another embodiment, the invention provides a computer-implemented method for evaluating a condition of a person, comprising:

determining at least one characteristic of a first facial expression of at least a mouth of the person, at a first time at which the person performs the first facial expression, based at least on a first image previously captured;

determining at least one characteristic of a second facial expression of at least a mouth of a person, at a second time at which the person performs the second facial expression, based at least on a second image previously captured, the first facial expression and the second facial expression being of a same first type of facial expression;

determining at least one difference between the at least one characteristic of the first facial expression determined and the at least one characteristic of the second facial expression determined; and generating an output signal indicating the condition of the person based at least on the at least one difference determined.

According to another embodiment, the invention provides a non-transitory computer-readable data storage medium storing executable program code configured to, when executed by at least one processor, perform at least:

determining at least one characteristic of a first facial expression of at least a mouth of a person, at a first time at which the person performs the first facial expression, based at least on a first image previously captured;

determining at least one characteristic of a second facial expression of at least a mouth of a person, at a second time at which the person performs the second facial expression, based at least on a second image previously captured, the first facial expression and the second facial expression being of a same first type of facial expression;

determining at least one difference between the at least one characteristic of the first facial expression determined and the at least one characteristic of the second facial expression determined; and generating an output signal indicating a condition of the person based at least on the at least one difference determined.

BRIEF DESCRIPTION OF THE DRAWINGS

The invention will be explained in greater detail with reference to exemplary embodiments depicted in the drawings is appended.

The accompanying drawings are included to provide a further understanding of the present invention and are incorporated in and constitute a part of this specification. The drawings illustrate the embodiments of the present invention and together with the description serve to explain the principles of the invention.

Other embodiments of the present invention and many of the intended advantages of the present invention will be readily appreciated as they become better understood by reference to the following detailed description.

Figure 1:
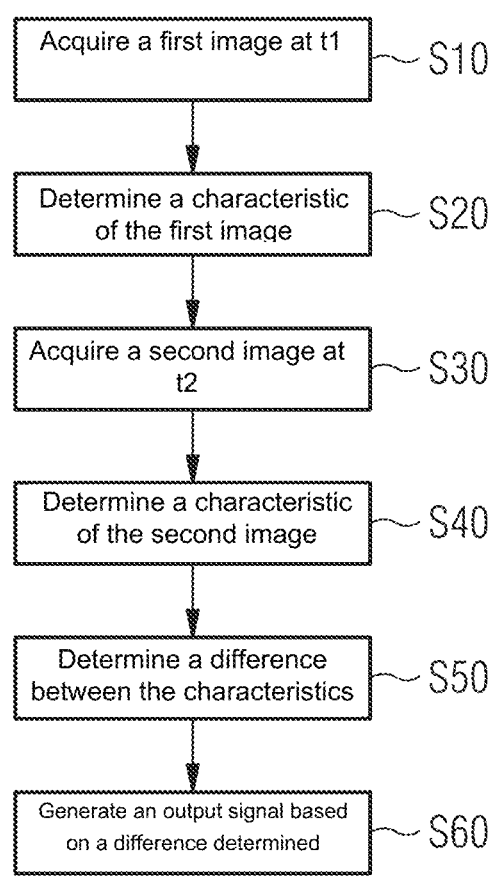
Figure 2:
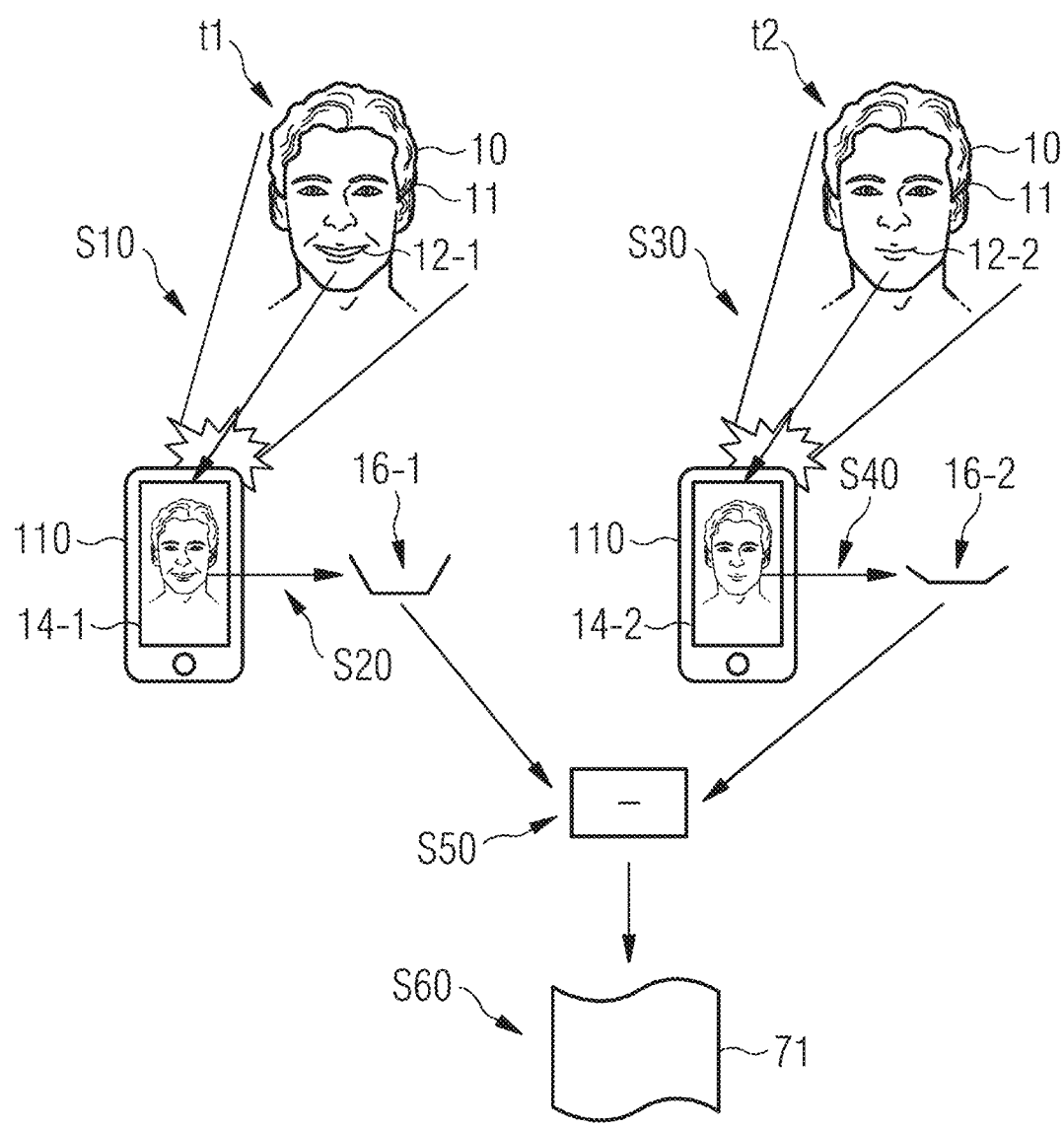
Figure 3:
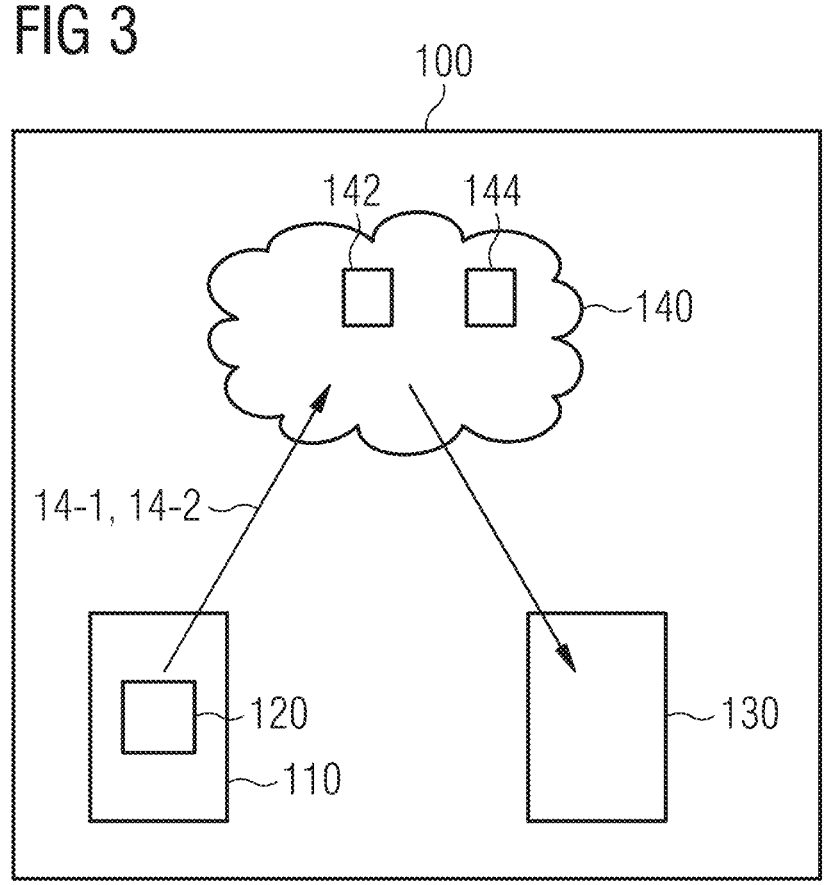
Figure 4:
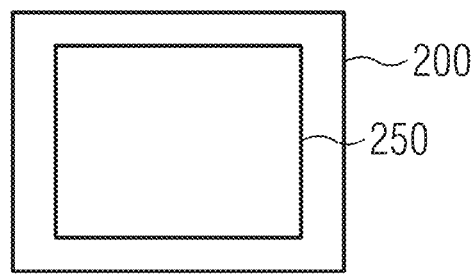
Figure 5:
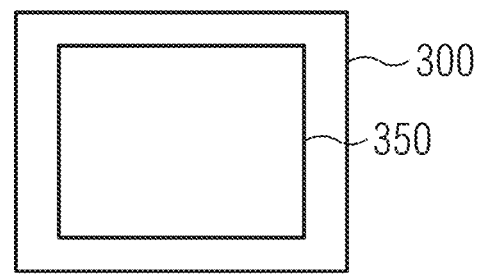

FIG. 1 shows a schematic flow diagram for illustrating a computer-implemented method for evaluating a person's condition according to a first embodiment;

FIG. 2 schematically illustrates the steps shown in FIG. 1;

FIG. 3 shows a schematic block diagram illustrating a system for evaluating a person's condition according to a second embodiment;

FIG. 4 shows a schematic block diagram of a non-transitory computer-readable data storage medium according to a third embodiment; and FIG. 5 shows a schematic block diagram of a computer program product according to a fourth embodiment.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to a first embodiment, the present invention provides a computer-implemented method for evaluating a condition of a person, comprising:

acquiring a first image of at least a mouth of a person at a first time at which the person is performing a first facial expression;

determining at least one characteristic of the first facial expression based at least on the acquired first image;

acquiring a second image of at least the mouth of the person at a second time at which the person is performing a second facial expression, wherein the first facial expression and the second facial expression are of the same first type of facial expression;

determining the at least one characteristic of the second facial expression based at least on the acquired second image;

determining at least one difference between the determined at least one characteristic of the first facial expression and the determined at least one characteristic of the second facial expression; and generating an output signal indicating the condition of the person based at least on the at least one determined difference.

In general, a facial expression is a manifestation of a type of a facial expression. In other words, a type of a facial expression can correspond to a genus of facial expressions (e.g. "smile", "neutral", "scream", "cry"), and a facial expression can correspond to a specific implementation of a type of a facial expression, in particular related to a person executing the facial expression at a certain time (in this sense "smile" can be considered as type of a facial expression, wherein "smile performed by certain person at certain time" can be considered as a facial expression being of the type of facial expression). The first type of facial expression comprises in a preferred embodiment a smile of the person. In this embodiment the first facial expression performed at the first time and the second facial expression performed at the second time are both a smiling facial expression performed by the person. Preferably, a second type of facial expression may comprise a neutral facial expression of the person.

The terminology "a first facial expression", "a second facial expression" and so on should be understood as terminology for differentiating facial expression instances of the same type or class (e.g. smile) the person produces at different times (or time points). The facial expression may be the same in all parameters such as shape, intensity and so on, or may be different. Acquiring an image "at a first time" or the like means that at least at that time an image is acquired, and does not exclude that a video is acquired, since a video comprises acquiring images at a plurality of times, or time points.

Preferably, the different time points (first time, second time and all optional additional time points) are time points on different days. It is unlikely for a patient's condition to change rapidly within one day, but from one day or another changes may be noticeable.

Preferably, determining the at least one characteristic based on an image comprises, or consists of, extracting the at least one characteristic from the image. However, in some advantageous embodiments, the at least one characteristic may be determined based on a plurality of images (e.g. based on a plurality of frames of a video).

The computer-implemented method may in particular be implemented by a mobile device, preferably a smartphone, running an application (or: app) configured to perform the method according to the first embodiment of the present invention.

The application may be configured to detect a time and date, and may further be configured to prompt a user to acquire an image every day (or every other day, or every third day or the like). For example, every day at the same time the application may send and/or display a notification to the user instructing the user to perform a facial expression of a specific type such as a smile and to acquire an image of the user's face while performing the facial expression of the respective type (e.g. smile). The application may provide additional instructions to the user, for example when to start smiling, how long to smile, to try to smile as hard as possible and so on.

According to a second embodiment, the present invention provides a system for evaluating a patient's condition, the system comprising:
an image capturing device configured to:
acquire a first image of at least a mouth of a person at a first time at which the person is performing a first facial expression and
acquire a second image of at least the mouth of the person at a second time at which the person is performing a second facial expression wherein the first facial expression and the second facial expression are of the first type of facial expression, in particular a smiling facial expression; and
a computing device configured to:
determine, based at least on the acquired first image, at least one characteristic of the first facial expression;
determine, based on at least the acquired second image, the at least one characteristic of the second facial expression;
determine a difference between the determined at least one characteristic of the first facial expression and the determined at least one characteristic of the second facial expression; and
generate an output signal indicating the condition of the person based at least on the determined difference.

The image capturing device may be a mobile device equipped with, or operatively connected to, a camera, a stationary device equipped with, or operatively connected to, a camera, and/or the like. Preferably, the image capturing device is a smartphone equipped with a front camera, i.e. a camera that can be used to take a picture of a user while the user is able to watch the display of the smartphone.

The computing device may be realized as any device, or any means, for computing, in particular for executing a software, an app, or an algorithm. For example, the computing device may comprise a central processing unit (CPU) and a memory operatively connected to the CPU. The computing device may also comprise an array of CPUs, an array of graphical processing units (GPUs), at least one application-specific integrated circuit (ASIC), at least one field-programmable gate array (FPGA), or any combination of the foregoing.

The computing device may be realized in a distributed way. For example, the computing device may comprise a processor of a mobile device as well as a cloud computing system, specifically a cloud computing platform and/or a cloud data storage. The computing device may also be implemented entirely by a cloud computing system.

The image capturing device, in particular the smartphone, may be provided with an app that is configured to perform at least one of the steps of an embodiment of the method according to the first embodiment, specifically the steps of acquiring a first image and/or of acquiring a second image. The app may be configured to communicate with a remote computing device, or a remotely arranged element of the computing device, for example with a cloud computing system.

In systems based on cloud computing technology, a large number of devices can be connected to a cloud computing system via the Internet. The devices may be located in a remote facility connected to the cloud computing system. For example, the devices can comprise, or consist of, sensors, actuators, robots, and/or medical devices in a healthcare unit. The devices can be home appliances such as mobile devices (smartphones, tablets and so on) or office appliances in a residential/commercial establishment.

The cloud computing system may enable remote configuring, monitoring, controlling, and maintaining connected devices (also commonly known as 'assets'). Also, the cloud computing system may comprise a cloud data storage which facilitates storing large amounts of data e.g. periodically gathered from the devices, analyzing the large amounts of data, and providing insights (e.g., Key Performance Indicators, Outliers) and alerts to operators, field engineers or owners of the devices via a graphical user interface (e.g., of web applications). The cloud computing system may also enable modifying parameters associated with the devices and issues control commands via the graphical user interface based on the insights and alerts.

The cloud computing system may comprise a plurality of servers or processors (also known as 'cloud infrastructure'), which are geographical distributed, connected with each other via a network. A dedicated platform (herein referred to as 'cloud computing platform') is installed on the servers/processors for providing computing power. The cloud computing platform may comprise a plurality of software programs executed on one or more servers or processors of the cloud computing system to enable delivery of requested services to the devices and its users.

According to a third embodiment, the invention provides a non-transitory computer-readable data storage medium comprising executable program code configured to, when executed, perform the method according to an embodiment of the first embodiment.

The storage medium may be a data storage like a magnetic storage/memory (e.g. magnetic-core memory, magnetic tape, magnetic card, magnet strip, magnet bubble storage, drum storage, hard disc drive, floppy disc or removable storage), an optical storage/memory (e.g. holographic memory, optical tape, Laserdisc, Phasewriter (Phasewriter Dual, PD), Compact Disc (CD), Digital Video Disc (DVD), High Definition DVD (HD DVD), Blu-ray Disc (BD) or Ultra Density Optical (UDO)), a magneto-optical storage/memory (e.g. MiniDisc or Magneto-Optical Disk (MO-Disk)), a volatile semiconductor/solid state memory (e.g. Random Access Memory (RAM), Dynamic RAM (DRAM) or Static RAM (SRAM)), a non-volatile semiconductor/solid state memory (e.g. Read Only Memory (ROM), Programmable ROM (PROM), Erasable PROM (EPROM), Electrically EPROM (EEPROM), Flash-EEPROM (e.g. USB-Stick), Ferroelectric RAM (FRAM), Magnetoresistive RAM (MRAM) or Phase-change RAM) or a data carrier/medium.

According to a fourth embodiment, the invention provides a computer program product comprising executable program code configured to, when executed, perform the method according to an embodiment of the first embodiment.

According to a fifth embodiment, the invention provides a data stream representing, or configured to provide, program code configured to, when executed, perform the method according to an embodiment of the first embodiment.

Further advantageous embodiments, variations and modifications will be presented in the dependent claims and in the description in combination with the figures.

In some advantageous embodiments, the determining of the at least one characteristic is performed using a trained machine learning entity, preferably a trained artificial neural network entity. The present invention therefore also provides a method for training a machine learning entity for use in the steps of the method according to the first embodiment. The use of machine learning entities are advantageous as they can be trained to determine even small differences in images which may be non-detectable by a person.

In some advantageous embodiments, a first characteristic of the at least one characteristic is a digital representation of a mouth line. A mouth line should be understood as the line formed by a lower contour of a person's upper lip and/or as the line formed by an upper contour of a person's lower lip, which coincide when the mouth of the person is not open. The mouth line thus exhibits comparatively large curvature when the facial expression (e.g. smile) is comparatively strong, and exhibits comparatively small curvature when the facial expression (e.g. smile) is comparatively weak.

The mouth line may be automatically determined e.g. based on geometrical objects recognized (e.g. using a trained machine learning entity) in the acquired image which are associated with the mouth line, for example, the corners of the mouth.

The digital representation of the mouth line may be any digital data format that quantifies properties of the mouth line. In some advantageous embodiments, the digital representation of the mouth line may be a polygonal line that approximates the mouth line, preferably using a predefined number of support points of the polygonal line.

In some advantageous embodiments, a second characteristic of the at least one characteristic is a state of at least one facial muscle of the person. Facial muscles can be used to describe in quantifiable ways the strength and scope of a facial expression, e.g. by binary numbers that indicate whether or not a certain facial muscle is contracted (0: not contracted; 1: contracted) or by numbers that indicate to which degree a certain facial muscle is contracted (0%: not contracted; x %: contracted to x %; 100%: maximally contracted). The state of a facial muscle may e.g. be determined by a depth analysis of an image or video, by a heat signature analysis of the muscle and/or the like.

It should be understood that the terms "first characteristic" and "second characteristic" (and so on) are used herein simply as designations and should not be construed to imply any priority, or that the "second characteristic" might only be used when also the "first characteristic" is used. In other words, in particular embodiments, the at least one characteristic may comprise, or consist of, only the first characteristic, only the second characteristic, both the first and the second characteristic etc. (optionally also for a third characteristic and so on).

In some advantageous embodiments, acquiring the first image and/or acquiring the second image comprises in each case acquiring a video of at least the mouth of the person, and determining one characterizing frame of the acquired video as the first image and/or second image to be acquired, respectively. The video may have a predetermined length, e.g. a length between 1 second and 15 seconds, preferable between 4 and 12 seconds, e.g. 10 seconds.

In other words, in some advantageous embodiments, acquiring the first image comprises acquiring a first video of at least the mouth of the person and determining one first characterizing frame of the acquired first video as the first image to be acquired;

and/or acquiring the second image comprises acquiring a second video of at least the mouth of the person and determining one second characterizing frame of the acquired second video as the second image to be acquired.

Preferably, the same method of acquiring images is used both in the case of the first and the second image (i.e. when the first image is acquired from a first video, then also the second image is acquired from a second video and so on).

Acquiring the first and/or second images from videos has the advantage that the content of the acquired image is less dependent on a particular moment in time but may be selected out of a plurality of frames of the acquired video instead.

In some advantageous embodiments, the characterizing frame is automatically determined based on a predefined criterion. In some advantageous embodiments, the predefined criterion is that the characterizing frame is a frame in which at least one of the at least one characteristic has an extremum, an average or a median within the acquired video. In this way, for example the facial expression of maximum strength of which the person was capable within the acquired video may be used. Associating the characterizing frame with the median of the at least one characteristic within the acquired video may lead to more consistent characteristics which may prevent false positive or false negatives.

As an alternative, the at least one characteristic may be determined based on not only one (first/second) image but on the entire (first/second) video. For example, the at least one characteristic may be determined for each frame (or for each frame of a random or predetermined selection of all frames), and the determined at least one characteristic may be determined to be an extremum, an average, or a median of the determined at least one characteristics of the frames.

The predefined criterion may itself comprise a plurality of sub-criteria connected by logical operators such as logical "AND" or "OR" and/or the like.

In some advantageous embodiments, a user is prompted to select one of the frames of the acquired video as the characterizing frame. The user may be the person itself, or alternatively the user may be a physician, a nurse or the like.

In some advantageous embodiments, a third characteristic of the at least one characteristic is a time from a starting frame of the acquired (first or second, respectively) video to the respective characterizing frame. For example, the characterizing frame that is determined as the first image or second image, respectively, may be determined by being the frame in which the captured facial expression of the person is strongest. Then, the third characteristic indicates a time span that was necessary for the person to reach the facial expression of maximum strength within the video.

In some advantageous embodiments, a first comparison image of at least the mouth of the person is acquired at the first time at which the person is performing a specific second type of facial expression, and determining of the at least one characteristic of the first facial expression is furthermore based on the acquired first comparison image. In other words, the first image is an image of the person performing (a first facial expression being) a first type of facial expressing, and the first comparison image is an image of the person performing a second type of facial expression. Acquiring the first image and the first comparison image at the first time is not to be understood that the first image and the first comparison image are acquired simultaneously, but subsequently within a timespan of e.g. up to ten minutes, preferably within a timespan of up to one minute. In an advantageous embodiment, the first type of facial expression is a smile, and the second type of facial expression is a neutral expression.

In particular, for both the first image and the first comparison image a digital representation of the mouth line can be determined, in particular by using a trained machine learning algorithm. The at least one characteristic of the first facial expression can then be based on both digital representations of the mouth line, in particular, the at least one characteristic of the first facial expression can be based on or comprise a difference of both digital representations of the mouth line.

In some advantageous embodiments, a second comparison image of at least the mouth of the person is acquired at the second time at which the person is performing a specific second type of facial expression, and determining of the at least one characteristic of the second facial expression is furthermore based on the acquired second comparison image. In other words, the second image is an image of the person performing (a second facial expression being) a first type of facial expressing, and the second comparison image is an image of the person performing a second type of facial expression. Acquiring the second image and the second comparison image at the second time is not to be understood that the second image and the second comparison image are acquired simultaneously, but subsequently within a timespan of up to ten minutes, preferably within a timespan of up to one minute. In an advantageous embodiment, the first type of facial expression is a smile, and the second type of facial expression is a neutral expression.

In particular, for both the second image and the second comparison image a digital representation of the mouth line can be determined, in particular by using a trained machine learning algorithm. The at least one characteristic of the second facial expression can then be based on both digital representations of the mouth line, in particular, the at least one characteristic of the second facial expression can be based on or comprise a difference of both digital representations of the mouth line.

By using a first and/or a second comparison image, the accuracy of the method, in particular the accuracy of the at least one characteristic of the first facial expression, or the accuracy of the difference of the at least one characteristic of the first facial expression and the at least one characteristic of the second facial expression, can be improved. In particular, changes in the muscular structure of the face, e.g. due to increasing age of the person, can be compensated.

In some advantageous embodiments, acquiring the first image and acquiring the first comparison image is executed by acquiring a video of at least the mouth of the person, in particular at the first time, by determining a first characterizing frame of the acquired video as the first image to be acquired, and by determining a second characterizing frame of the acquired video as the first comparison image to be acquired. In particular, the first and the second characterizing frame can be determined automatically, e.g. by choosing frames with extremal properties (e.g. the maximum smile and the most neutral face expression).

In some advantageous embodiments, acquiring the second image and acquiring the second comparison image is executed by acquiring a video of at least the mouth of the person, in particular at the second time, by determining a first characterizing frame of the acquired video as the second image to be acquired, and by determining a second characterizing frame of the acquired vides as the second comparison image to be acquired. In particular, the first and the second characterizing frame can be determined automatically, e.g. by choosing frames with extremal properties (e.g. the maximum smile and the most neutral face expression).

By determining the first image and the first comparison image based on the same video, and/or by determining the second image and the second comparison image based on the same video, in each case only one interaction with the user is necessary, improving the speed of the method as well as the usability.

In some advantageous embodiments, determining of the at least one characteristic of the second facial expression is furthermore based on the acquired first comparison image. In other words, all further images acquired at later times can be compared with the first comparison image. By this comparison, the accuracy of the method can be improved, while at the same time reducing the amount of data to be processed and number or time of interactions with the person.

In some advantageous embodiments, after the first image and the second image, further images at further times at which the person is performing further specific facial expressions of the same type, in particular smiles, respectively, are acquired within a respective predetermined interval from one another. The predetermined interval may be set to one or more days, e.g. to one day, two days, three days, a week, or the like.

Based on each of the further images the at least one characteristic of the respective further facial expression in the corresponding further image is determined, e.g. a digital representation of the mouth line is determined (or: extracted) from each of the further images, characterizing in each case a specific facial expression such as a smile is performed by the user in the respective further image.

Preferably, at least one further difference between the determined at least one characteristic of the further specific facial expression such as a smile and at least one respective previously determined at least one characteristic is determined, and the output signal is additionally based on the at least one further difference. For example, the difference of each of the at least one determined characteristics to the at least one determined characteristic of the first specific facial expression (such as the first smile or first neutral facial expression) may be determined, and a trend may be determined and/or an extrapolation may be performed.

Preferably, for each of the further images a further comparison image is acquired, and the at least one characteristic of the respective further image is furthermore based on the respective further comparison image, preferably in a similar way as for the at least one characteristic of the first image. Preferably, the further image and the further comparison image can be extracted from the same video.

In some advantageous embodiments, the acquired first image and the acquired second image (and optionally any further acquired images) are stored in a cloud data storage of a cloud computing system. In this way, none of the acquired images is lost, or can be manipulated.

The determining of the at least one characteristic of the first facial expression and the determining of the at least one characteristic of the second facial expression (and optionally the determining of characteristics of further facial expressions in further acquired images) are performed by a cloud computing platform of the cloud computing system. In this way, there is always sufficient computing power available for the determining.

In some advantageous embodiments, the determined at least one characteristic of the first facial expression and the determined at least one characteristic of the second facial expression (and optionally any characteristics further determined for further specific facial expressions in further acquired images) are stored in a cloud data storage of a cloud computing system. In this way, the information contained in the acquired images may be stored and saved instead of, or in addition to, the acquired images themselves. Moreover, the characteristics will in general consume less data storage space so that storing the characteristics instead of the acquired images themselves may serve to reduce the necessary data storage space.

The determining of the at least one difference between the determined at least one characteristic of the first specific facial expression and the determined at least one characteristic of the second specific facial expression of the same type such as a smile (and optionally the determining of further differences) is preferably performed by a cloud computing platform of the cloud computing system. In this way, there is always sufficient computing power available for the determining of the difference.

In some advantageous embodiments, the generating of the output signal is performed by a cloud computing platform of a cloud computing system. The generated output signal may be sent to the image capturing device and/or to a different receiving device. More than one output signal may be generated, and the output signal (or any or each of the output signals) may be realized as comprising, or consisting of, control signals.

Preferably, the determining of the at least one characteristic, the determining of the at least one difference and/or the generating of the output signal may be performed by the same cloud computing system, in particular by the same cloud computing platform.

Although various advantageous options, variants and embodiments have been described in the foregoing with respect to the method according to the first embodiment of the present invention, it should be understood that the same options, variants and embodiments also equally apply to the system according to the second embodiment.

FIG. 1 shows a schematic flow diagram for illustrating a computer-implemented method for evaluating a patient's condition according to an embodiment of the present invention.

The method of FIG. 1 is further explained with reference to FIG. 2 which schematically illustrates the steps as listed in FIG. 1 in order to facilitate understanding.

Furthermore, reference will also be made to FIG. 3 which shows a schematic block diagram illustrating a system 100 for evaluating a person's condition according to a second embodiment.

The method according to FIG. 1 will in the following be described specifically in combination with a mobile device (such as a smartphone, a tablet or the like) which executes an application (or: app) configured to perform the method. It should be understood that the method may be performed also in other ways and by other types of image capturing devices. For example, instead of a mobile device, a desktop PC operatively connected to a camera may be used, optionally further operatively connected to a cloud computing system.

In a step S10, a first image 14-1 of at least a mouth, preferably a face 11, of a person 10 at a first time t1 is acquired, the first time t1 being a time at which the person 10 is performing a first facial expression 12-1 the person 10 can be a patient whose health is investigated by another person or by the person 10 itself using the computer-implemented method of the present invention. Acquiring the first image 14-1 of the complete face 11 of the person 10 instead of just of the mouth has the advantage that further processing of the image is simplified as such features as an orientation of the mouth may e.g. be automatically determined from the orientation of the eyes and/or ears of the face 11. The first facial expression 12-1 is of a first type of facial expression, in particular a smiling facial expression as also illustrated in FIG. 2. The first facial expression is not limited to a smiling facial expression but can also comprise other facial expressions. The first facial expression is of a first type of facial expressions which can comprise besides a smiling facial expression also a screaming facial expression, a crying facial expression, a frowning facial expression. A second type of facial expression can comprise a neutral facial expression with a straight horizontal line between the lips of the person 10 which can facilitate the detection of characteristics because it allows normalization using a baseline.

The first image 14-1 may be acquired specifically using a camera of a mobile device 110. This may be prompted by an app stored in a memory of the mobile device 110 and executed by a central processing unit, CPU, of the mobile device 110.

As has been described, the app may be designed to help a person to determine symptoms of Parkinson's Disease, in particular to determine a reduced strength of facial expressions.

The method may comprise (and the app may be designed accordingly) a step of prompting the person every day to acquire an image, in particular acquiring the image using a camera of the mobile device 110. The app may have at least partially control over the camera of the mobile device 110 and may require, or allow, the images to be taken by the camera while the camera is being controlled by the app.

Preferably, the camera of the mobile device 110 used in the present method is a front camera (or a so-called selfie camera), i.e. a camera that allows to acquire an image of a user while the user is able to watch the display of the mobile device 110, e.g. in order to follow instructions given therein, or in order to review the image currently being acquired. In this way, lighting issues, framing issues and so on of the image currently being acquired can be resolved by the user in real-time.

In the following, the method will be described for a case in which a user of the mobile device 110 is also the person whose condition is to be evaluated. However, it will be understood that the method is equally applicable in the case that a user of the mobile device 110 uses the mobile device 110 in order to evaluate the condition of another person 10, for example a person 10 that cannot, or does not want to, use the mobile device 110.

Optionally, the method may comprise a step of giving the user additional information about how to acquire the image, and the app may be designed accordingly. For example, instructions could be given to the user in sequence, each after the previous instruction has been fulfilled, e.g.:

1. "Please switch your mobile device to the front camera"
2. "Please position your face completely within the picture"
3. "Please perform a facial expression of a first type (e.g. smiling facial expression) as hard as you can" (Request for a specific facial expression of a certain type)
4. "Please press the 'Take Picture' button now".

In this way, the method may provide a guided human-machine interaction such that the user correctly operates the image capturing device (here: mobile device 110) in order to acquire an optimal image that can then be processed in an optimal way.

Accordingly, acquiring the first image 14-1 may be implemented by the user, either by himself/herself or guidedly, taking a picture of himself/herself, e.g. by pressing a "Take Picture" button on the graphical user interface, GUI, of the app.

In some advantageous embodiments, acquiring the first image 14-1 comprises (preferably again using the camera, in particular the front camera, of a mobile device 110) acquiring a first video of at least the mouth, preferably the face 11, of the person 10 and determining one characterizing frame of the acquired video as the first image 14-1. Expressed in another way, a time point within the acquired (or: recorded) video is determined to be the first time t1, namely the time point at which the characterizing frame was produced by the camera.

The method (and, preferably, the app) may be implemented such that the characterizing frame is determined automatically, or such that it is determined manually by a user, or such that it is determined in a guided human-machine interaction in which the app guides the user to select one of the frames of the acquired video as the characterizing frame (or, equivalently, to select one of the time points within the video as the first time).

The method may also be implemented such (and the app accordingly) that the user is given the choice how the characterizing frame should be determined, i.e. between an automatic mode in which the characterizing frame is determined automatically, and between a manual mode (and/or a guided mode) in which the user is prompted to select one of the frames of the acquired first video as the characterizing frame.

In cases or modes in which the characterizing frame is to be determined automatically, the characterizing frame is determined automatically based on at least one predefined criterion, as will be explained in more detail in the following.

In cases or modes in which the user is prompted to select one of the frames of the acquired first video as the characterizing frame, the app may provide the user with at least one suggested frame (e.g. determined in the same way as the characterizing frame would have been detected automatically in the automatic mode) which the user may then have the opportunity to accept or to replace by another frame, e.g. by clicking a button or performing a touch gesture on a touch screen of the mobile device 110.

In a step S20, at least one characteristic 16-1 of the first facial expression 12-1 (such as a smiling, screaming, crying or frowning facial expression) is determined based on (e.g. extracted from) the acquired first image 14-1. The at least one characteristic 16-1 may in particular be determined (i.e. the determining S20 may be performed) by a machine learning entity. The trained machine learning entity can comprise a trained machine learning function or trained machine learning algorithm executed on an execution engine or processor. The trained machine learning entity can comprise a function or algorithm trained based on machine learning. The trained machine learning entity can comprise a trained artificial neural network, in particular a trained deep convolutional neural network, CNN.

In the presently described embodiment the at least one characteristic 16-1 comprises a digital representation of a mouth line of the first facial expression 12-1 (such as a smiling, screaming, crying or frowning facial expression). It should be understood, however, that also another characteristic may be used, e.g. a state (relaxed/contracted, or relaxed/contracted to degree x %/fully contracted) of a facial muscle of the person 10, preferably a state of each of a predefined plurality of facial muscles.

It should also be understood that both the digital representation 16-1 of the mouth line of the first facial expression (e.g. smile) 12-1 as well as the state of at least one facial muscle of the person 10 (optionally combined with further characteristics) may be used as the at least one characteristic to be determined.

The at least one characteristic of a first facial expression 12-1 which can comprise a digital representation of the mouth line of a mouth in the face 11 of the person 10 is preferably determined based on (more preferably extracted from) the acquired first image 14-1 by a trained artificial neural network entity trained with training data e.g. in supervised learning in which images of mouths (or of faces) are labelled (or: associated) with corresponding digital representations of mouth lines.

The digital representation of the mouth line may e.g. be given by a polygonal line, e.g. by a polygonal line with a predefined number of support points (i.e. points at which the polygonal line is allowed to be non-differentiable, or, in other words, points at which the polygonal lines may have, but does not have to have, a kink).

The artificial neural network, ANN, entity may be trained to receive, as its input, pictures including a mouth of a person and to produce as its output polygonal lines. Training the artificial neural network entity to produce polygonal lines with a fixed number of support points may result in easier comparison between different polygonal lines (i.e. between different digital representations of the mouth line) as will be discussed in the following. The artificial neural network, ANN, entity can comprise a deep convolutional neural network, CNN.

It should be understood that in the case of other characteristics to be determined based on (preferably extracted from) the acquired first image 14-1, the trained artificial neural network, ANN, entity will be trained to produce other measures for characterizing the first facial expression 12-1 of the first type, for example to produce for each facial muscle of a predetermined set of facial muscles a value indicating to which degree the muscle is contracted. In that case, the output layer of the trained artificial neural network, ANN, entity may comprise a number of output nodes equal to the number of facial muscles in the predetermined set of facial muscles.

The trained machine learning entity, in particular the trained artificial neural network, ANN, entity, may be implemented by the mobile device 110; however, it is preferably implemented by a cloud computing device as will be described in the following. Cloud computing devices generally offer larger computing power than mobile devices and can easily implement trained machine learning entities which can be continuously trained.

In a step S30, a second image 14-2 of at least the mouth (preferably of the face 11) of the person 10 at a second time t2 at which the person 10 is performing a second facial expression (of the same specific first type such as smile) 12-2 is acquired.

Step S30 may be performed in the same way as has been described in the foregoing with respect to step S10. In particular, step S30 may be performed by the described app being run by a mobile device 110. As has been mentioned, the app may be designed to prompt a user to acquire (or: to take) a picture (or video) of the mouth of the person 10 (or a picture of the face 11 of the person 10) on each day, or according to another temporal interval, e.g., every two days, every three day, every week, and so on.

Thus, step S10 of acquiring the first image 14-1 may be performed in a first of consecutive temporal intervals (e.g. on day 1), step S30 of acquiring the second image 14-2 may be performed in a second of the consecutive temporal intervals (e.g. on day 2), and optionally further steps of acquiring further images may be performed in further consecutive temporal intervals (e.g. on day 3, day 4, and so on). It should be understood that also the further steps as will be described in the following may then advantageously be performed also for these further images such that a daily (or weekly etc.) monitoring of the person's condition is provided.

The digital images 14-1, 14-2 acquired in steps S10, S30 (and optionally in further acquiring steps at further times) are preferably stored for further processing. The acquired images 14-1, 14-2 may be stored in the mobile device 110 that has been used to acquire them. However, the acquired images 14-1, 14-2 may also be automatically transmitted to a cloud data storage of a cloud computing system for storing.

In this way, the acquired images 14-1, 14-2 are safe from accidental deletion as well as from manipulation. Moreover, the acquired images 14-1, 14-2 stored in the cloud data storage may be used for unsupervised training of a machine learning entity. The storing of the acquired images 14-1, 14-2 may be performed automatically in the background so that the user of the mobile device 110 does not have to put any thought into this task.

FIG. 3 schematically shows a system 100 according to the second embodiment, which comprises an image capturing device, here a mobile device 110, configured for performing at least steps S10 and S30 (and optionally the further steps of acquiring further images at further times). The mobile device 110 is further configured to communicate with a cloud computing system 140 of the system 100, in particular to transmit the acquired images 14-1, 14-2 and/or the determined characteristics to a cloud data storage 144 of the cloud computing system 140.

In a step S40, the at least one characteristic is determined based on (preferably extracted from) the acquired second image 14-2, for example, an at least one characteristic 16-2 of the second facial expression 12-2 can comprise a digital representation 16-2 of the mouth line of the second facial expression 12-2, e.g. by a polygonal line. As has already been mentioned in the foregoing, the determining S20 as well as the determining S40 may be performed by the cloud computing system 140, in particular by a cloud computing platform 142 of the cloud computing system 140.

The mobile device 110 may comprise a processor 120 which is operatively coupled to an internal data storage of the mobile device 110. The processor 120 may be part of a computing device that is configured to perform at least one of the steps of the presently described method, e.g. step S20 and step S40.

In addition, or as an alternative, to the storing of the acquired images 14-1, 14-2 in the cloud data storage 144, the determined at least one characteristic of the facial expressions 12-1, 12-2 may be stored in the cloud data storage 144.

In a step S50, at least one difference between the determined at least one characteristic 16-1 of the first facial expression (e.g. smile) 12-1 and the determined at least one characteristic 16-2 of the second facial expression (e.g. smile) 12-2 is determined. Optionally, further differences between further smiles in further images acquired at further time points may be determined.

Step S50 may be performed by the mobile device 110; however, step S50 is preferably performed by the cloud computing platform 142 due to its superior computing power. The cloud computing platform 142 may thus have access to the acquired images 14-1, 14-2 and/or the determined characteristics which are preferably stored at the cloud data storage 144.

If the at least one characteristic has been determined of smiles of a plurality of more than three facial expressions of the same type (e.g. smile) (each determined based on a corresponding image at a corresponding time), then differences from the at least one characteristic of each facial expression of the respective specific first type (e.g. smile) to the at least one characteristic of the first facial expression 12-1 of the respective first type and/or differences from the at least one characteristic of each facial expression of the same first type (e.g. smile) to the at least one characteristic of the immediately preceding facial expression of the first type (e.g. smile) may be automatically determined.

"Immediately preceding" here means acquired at a time which is the directly previous time at which an image has been acquired. For example, for a smile determined based on a third image acquired at a third time (e.g. day 3), the immediately preceding facial expression of the specific predetermined type is the second facial expression 12-2 of the specific first type (e.g. smile) which has been determined based on the second image 14-2 acquired at the second time t2 (e.g. day 2), and so on.

The differences to the at least one characteristic 16-1 of the first facial expression 12-1 of the first type (e.g. smile) enables to track the changes compared to the first facial expression 12-1 which is used as a sort of benchmark or base line. When the first facial expression 12-1 is taken by the person 10 when it is healthy, then the differences of the at least one characteristic of the facial expressions of the same first type determined based on later images at later times to the at least one characteristic 16-1 of the first facial expression 12-1 can reliably indicate a deterioration of the person's 10 health.

In the case that the at least one characteristic 16-1, 16-2 of the first and second facial expression 12-1, 12-2 are formed by digital representations 16-1, 16-2 of the mouth line of the person 10 in the form of polygonal lines as the characteristic to be determined, the onset of e.g. facial bradykinesia can be noted by the straightening out of the polygonal lines.

In order to determine the difference between two polygonal lines, the two polygonal lines may be automatically arranged such that the sum of distances (or sum of squared distances or the like) between corresponding points in the two polygonal lines (i.e. first point of the first polygonal line to first point of the second polygonal line, second point of the first polygonal line to second point of the second polygonal line and so on until last point of the first polygonal line to last point of the second polygonal line) are minimized. That minimized sum may then be provided as a measure of the difference between the two polygonal lines.

In the foregoing it has been mentioned that a characterizing frame of an acquired video may be automatically determined based on a predefined criterion in steps S10, S30. In these steps, for each frame (or for a random or regular selection out of all frames) the corresponding at least one characteristic 16-1 of the first facial expression 12-1 captured therein may be determined, and the criterion for determining the characterizing frame may be based on the determined at least one characteristic of the first facial expression (e.g. smile) in each of the frames. For example, as characterizing frame a frame may be selected which has an extremal characteristic, i.e. the highest or lowest of the at least one characteristic 16-1.

In order to determine the characterizing frame, the acquired videos may be sent to the cloud computing platform 142, and the characterizing frame may be determined by the cloud computing platform 142. In that case, the first image 14-1 (and the second image 14-2 and so on) is acquired by the mobile device 110 but is determined as such and isolated from the other frames (which are not the characterizing frame), only by the cloud computing platform 142. In some variants, the characterizing frame determined by the cloud computing platform 142 as the first image 14-1 may be sent to the mobile device 110 so that the user of the mobile device 110 may review it and approve or disapprove of it and/or store it within the mobile device 110. In a possible embodiment, facial expressions of the same person 10 but of different facial expression types such as a smile and neutral facial expressions can be extracted from the same video (e.g. as extreme positions).

In a step S60, an output signal 71 indicating the condition of the person 10 based at least on the at least one determined difference is generated, preferably by the cloud computing platform 142. The output signal 71 may be transmitted to the mobile device 110 and may control the app run by the mobile device 110. The output signal 71 may, additionally or alternatively, be transmitted to a receiving device 130 (see FIG. 3) of the system 100 which may be a device accessible by a physician or a digital health services provider. The receiving device 130 may also be a mobile device. The output signal 71 is displayed in an embodiment on a display unit.

The receiving device 130 may be configured to run an app that is configured to receive output signals 71 of a plurality of apps of a plurality of mobile devices 110 of a plurality of persons, and to inform a user of the receiving device when any one of the received output signals 71 indicates a warning mode.

As an example, in step S60 a comparison of the determined at least one difference with at least one corresponding predefined threshold may be performed, and when the at least one determined difference exceeds the at least one corresponding threshold, the output signal 71 is generated such as to indicate a warning. The output signal 71 can be displayed on a display unit.

For example, in the case of polygonal lines discussed above, when the minimized sum acting as measure of the difference between the polygonal lines exceeds a predefined threshold value, the output signal 71 is generated as a warning signal, or as indicating a warning mode. When the sum does not exceed the predefined threshold, either no output signal 71 is generated, or an output signal 71 indicating a normal mode may be generated.

An output signal 71 indicating a normal mode may be configured to control the app run by the mobile device 110 (and/or an app of the receiving device 130) to continue as has been described in the foregoing. By contrast, an output signal 71 indicating a warning mode may control the app run by the mobile device 110 (and/or an app of the receiving device 130) to change into the warning mode. In the warning mode, the app may suggest to a user or the person 10 that a visit to a physician would be advisable, or that another image for confirmation should be taken, and/or may instruct the user or the person 10 to perform an exercise.

The method as illustrated in FIGS. 1, 2 comprising steps S10 to S60 can be executed entirely on a processing unit of a device, in particular a mobile device 110.

In a possible embodiment a first comparison image of at least the mouth of the person 10 is acquired at the first time at which the person 10 is performing a specific second type of facial expression. The second type of facial expression can comprise a neutral facial expression of the person 10 with straight lips. In this embodiment the determining of the at least one characteristic of the first facial expression 12-1 in step S20 can also be based on the acquired first comparison image.

In a further possible embodiment, a second comparison image of at least the mouth of the person 10 is acquired at the second time at which the person 10 is performing the second type of facial expression. In this embodiment the determining of the at least one characteristic of the second facial expression 12-2 in step S40 can also be based on the acquired second comparison image. Such a characteristic can be for instance a distance of a corner of the mouth of the person 10 when smiling from the corner of the mouth of the person 10 in a basic facial expression state, in particular a neutral facial expression type with closed straight horizontal lips.

The first image 14-1, the second image 14-2 as well as the first and second comparison images can be extracted in a possible embodiment from the same video of at least the mouth of the person 10.

The first comparison image of at least the mouth of the person 10 is acquired at the first time at which the person 10 is performing a specific second type of facial expression. Determining of the at least one characteristic 16-1 of the first facial expression 12-1 in step S20 can be furthermore based on the acquired first comparison image. In other words, the first image 14-1 is an image of the person 10 performing (a first facial expression being) a first type of facial expression (e.g. smile), and the first comparison image is an image of the person 10 performing a second type of facial expression (e.g. neutral facial expression). Acquiring the first image 14-1 and the first comparison image at the first time is not to be understood that the first image 14-1 and the first comparison image are acquired simultaneously, but subsequently within a timespan of e.g. up to ten minutes, preferably within a timespan of up to one minute. In a possible embodiment, the first type of facial expression is a smiling facial expression and the second type of facial expression is a neutral facial expression.

In particular, for both the first image 14-1 and the first comparison image a digital representation of the mouth line of the mouth of the person 10 can be determined, in particular by using a trained machine learning algorithm. The at least one characteristic of the first facial expression can then be based on both digital representations of the mouth line, in particular, the at least one characteristic of the first facial expression can be based on or comprise a difference of both digital representations of the mouth line of the mouth of the person 10.

In a possible embodiment, a second comparison image of at least the mouth of the person 10 is acquired at the second time at which the person 10 is performing a specific second type of facial expression. Determining the at least one characteristic of the second facial expression 12-2 in step S40 can furthermore be based on the acquired second comparison image. In other words, the second image is an image of the person 10 performing a second type of facial expression. Acquiring the second image 14-2 and the second comparison image at the second time is not to be understood that the second image 14-2 and the second comparison image are acquired simultaneously, but subsequently within a time span of e.g. up to ten minutes, preferably within a timespan of up to one minute. In a possible embodiment, the first type of facial expression is a smiling facial expression, and the second type of facial expression is a neutral facial expression of the face of the person 10.

In particular, for both the second image and the second comparison image a digital representation of the mouth line can be determined, in particular by using a trained machine learning algorithm. The at least one characteristic of the second facial expression can be based on both digital representations of the mouth line, in particular, the at least one characteristic of the second facial expression can be based on or comprise a difference of both digital representations of the mouth line of the mouth of the person 10.

By using a first and/or second comparison image, the accuracy of the method, in particular the accuracy of the at least one characteristic of the first facial expression, or the accuracy of the difference of the at least one characteristic of the first facial expression and the at least one characteristic of the second facial expression, can be improved. In particular, changes in the muscular structure of the face of the person 10, e.g. due to increasing age of the person 10, can be compensated.

In a possible embodiment, acquiring the first image and acquiring the first comparison image is executed by acquiring a video of at least the mouth of the person 10, in particular at the first time, by determining a first characterizing frame of the acquired video as the first image to be acquired, and by determining a second characterizing frame of the acquired video as the first comparison image to be acquired. In particular, the first and the second characterizing frame can be determined automatically, e.g. by choosing frames with extreme properties (e.g. the maximum smile and the most neutral face expression).

In some embodiments, acquiring the second image 14-2 and acquiring the second comparison image is executed by acquiring a video of at least the mouth of the person 10, in particular at the second time, by determining a first characterizing frame of the acquired video as the second image to be acquired, and by determining a second characterizing frame of the acquired vides as the second comparison image to be acquired. In particular, the first and the second characterizing frame can be determined automatically, e.g. by choosing frames with extreme properties (e.g. a maximum smile with maximal curved lips and a most neutral face expression with lips as straight as possible).

By determining the first image and the first comparison image based on the same video, and/or by determining the second image and the second comparison image based on the same video, in each case only one interaction with a user or person 10 is necessary, improving the evaluation speed of the method as well as its usability.

In some embodiments, determining of the at least one characteristic of the second facial expression 12-2 is furthermore based on the acquired first comparison image. In other words, all further images acquired at later times can be compared with the first comparison image. By this comparison, the accuracy of the method can be improved, while at the same time reducing the amount of data to be processed and number or time of interactions with the person 10.

FIG. 4 shows a schematic block diagram of a non-transitory computer-readable data storage medium 200 comprising executable program code 250 configured to, when executed, perform the method according to the first embodiment, in particular the method as described in the foregoing with respect to FIG. 1 to FIG. 3.

FIG. 5 shows a schematic block diagram of a computer program product 300 comprising executable program code 350 configured to, when executed, perform the method according to the first embodiment, in particular the method as described in the foregoing with respect to FIG. 1 to FIG. 3.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for evaluating a condition of a person, comprising:
    acquiring a first image of at least a mouth of the person at a first time at which the person performs a first facial expression;
    determining at least one characteristic of the first facial expression based at least on the first image acquired;
    acquiring a second image of at least the mouth of the person at a second time at which the person performs a second facial expression, the first facial expression and the second facial expression being of a same first type of facial expression;
    determining at least one characteristic of the second facial expression based at least on the second image acquired;
    determining at least one difference between the at least one characteristic of the first facial expression determined and the at least one characteristic of the second facial expression determined; and
    generating an output signal indicating the condition of the person based at least on the at least one difference determined,
    wherein at least one of the acquiring of the first image and the acquiring of the second image includes acquiring a video of at least the mouth of the person and determining a characterizing frame of the video acquired as at least one of the first image acquired and the second image acquired, and
    wherein one of
        the characterizing frame of the video acquired is automatically determined based on a criterion, or
        a user or the person is prompted to select one of the frames of the video acquired as the characterizing frame.

2. The computer-implemented method of claim 1, wherein of at least one of the determining of the at least one characteristic of the first facial expression and the determining of the at least one characteristic of the second facial expression, is performed using a trained machine learning entity.

3. The computer-implemented method of claim 1, wherein at least one of a first characteristic of the at least one characteristic of the first facial expression and a first characteristic of the at least one characteristic of the second facial expression is a digital representation of a mouth line of the mouth of the person.

4. The computer-implemented method of claim 3, wherein at least one of a second characteristic of the at least one characteristic of the first facial expression and a second characteristic of the at least one characteristic of the second facial expression is a state of at least one facial muscle of the person.

5. The computer-implemented method of claim 1, wherein the criterion is that the characterizing frame is a frame in which at least one of the at least one characteristic of the first facial expression and at least one characteristic of the second facial expression has an extremum, an average or a median within the video acquired.

6. The computer-implemented method of claim 1, further comprising:
acquiring a first comparison image of at least the mouth of the person at the first time at which the person performs a specific second type of facial expression, wherein the determining of the at least one characteristic of the first facial expression is additionally based on the first comparison image acquired.

7. The computer-implemented method of claim 6, wherein the acquiring of the first image and the acquiring of the first comparison image comprises:
acquiring a video of at least the mouth of the person;
determining a first characterizing frame of the video acquired as the first image to be acquired; and
determining a second characterizing frame of the video acquired as the first comparison image to be acquired.

8. The computer-implemented method of claim 1, wherein a third characteristic of the at least one characteristic of the first facial expression and the at least one characteristic of the second facial expression is a time from a starting frame of the video acquired, to the frame determined as the respective first image or second image.

9. The computer-implemented method of claim 1, wherein after the first image and the second image, further images at further times at which the person is performing further facial expressions of the same first type of facial expression are acquired within a respective time interval from one another;
wherein, based on each of the further images, the at least one characteristic of each of respective further facial expression in a corresponding respective further image of the further images, is determined;
wherein at least one further difference between the determined at least one characteristic of the further facial expressions and at least one respective previously determined at least one characteristic is determined; and
wherein the output signal is additionally based on the at least one determined further difference.

10. The computer-implemented method of claim 1, wherein at least one of
the first type of facial expression type comprises at least one of a smiling facial expression, a crying facial expression, a screaming facial expression or a frowning facial expression and the second type of facial expression comprises a neutral facial expression of the person.

11. A non-transitory computer-readable data storage medium storing executable program code configured to, when executed by at least one processor, perform the method of claim 1.

12. A system for evaluating a condition of a person, comprising:
an image capturing device configured to:
acquire a first image of at least a mouth of the person at a first time at which the person performs a first facial expression, and
acquire a second image of at least the mouth of the person at a second time at which the person performs a second facial expression, the first facial expression and the second facial expression being of a same first type of facial expression,
wherein the image capturing device, to acquire at least one of the first image and at least one of the second image, is configured to acquire a video of at least the mouth of the person; and
a computing device configured to:
determine, based at least on the first image acquired, at least one characteristic of the first facial expression;
determine, based on at least the second image acquired, the at least one characteristic of the second facial expression;
determine a difference between the at least one characteristic of the first facial expression determined and the at least one characteristic of the second facial expression determined; and
generate an output signal, indicating the condition of the person based at least on the difference determined,
wherein the computing device is further configured to determine a characterizing frame of the video acquired as at least one of the first image acquired and the second image acquired, and
wherein one of
the computing device is further configured to determine the characterizing frame of the video acquired, automatically, based on a criterion, or
the computing device is further configured to prompt a user or the person to select one of the frames of the video acquired as the characterizing frame.

13. The system of claim 12, further comprising:
an interface, to output the output signal.

14. The system of claim 12, wherein the criterion is that the characterizing frame is a frame in which at least one of the at least one characteristic of the first facial expression and at least one characteristic of the second facial expression has an extremum, an average or a median within the video acquired.

15. The system of claim 12, wherein a third characteristic of the at least one characteristic of the first facial expression and the at least one characteristic of the second facial expression is a time from a starting frame of the video acquired, to the frame determined as the respective first image or second image.

16. A computer-implemented method for evaluating a condition of a person, comprising:
determining at least one characteristic of a first facial expression of at least a mouth of the person, at a first time at which the person performs the first facial expression, based at least on a first image previously captured;
determining at least one characteristic of a second facial expression of at least a mouth of a person, at a second time at which the person performs the second facial expression, based at least on a second image previously captured, the first facial expression and the second facial expression being of a same first type of facial expression;

determining at least one difference between the at least one characteristic of the first facial expression determined and the at least one characteristic of the second facial expression determined; and generating an output signal indicating the condition of the person based at least on the at least one difference determined, wherein at least one of previously capturing of the first image and previously capturing of the second image includes previously capturing a video of at least the mouth of the person and determining a characterizing frame of the video acquired as at least one of the first image acquired and the second image acquired, and wherein one of
- the characterizing frame of the video acquired is automatically determined based on a criterion, or
- a user or the person is prompted to select one of the frames of the video acquired as the characterizing frame.

17. The computer-implemented method of claim 16, wherein of at least one of the determining of the at least one characteristic of the first facial expression and the determining of the at least one characteristic of the second facial expression, is performed using a trained machine learning entity.

18. The computer-implemented method of claim 16, wherein the criterion is that the characterizing frame is a frame in which at least one of the at least one characteristic of the first facial expression and at least one characteristic of the second facial expression has an extremum, an average or a median within the video acquired.

19. The computer-implemented method of claim 16, wherein the criterion is that the characterizing frame is a frame in which at least one of the at least one characteristic of the first facial expression and at least one characteristic of the second facial expression has an extremum, an average or a median within the video acquired.

20. The computer-implemented method of claim 16, wherein a third characteristic of the at least one characteristic of the first facial expression and the at least one characteristic of the second facial expression is a time from a starting frame of the video acquired, to the frame determined as the respective first image or second image.

21. A non-transitory computer-readable data storage medium storing executable program code configured to, when executed by at least one processor, perform at least:

determining at least one characteristic of a first facial expression of at least a mouth of a person, at a first time at which the person performs the first facial expression, based at least on a first image previously captured;

determining at least one characteristic of a second facial expression of at least a mouth of a person, at a second time at which the person performs the second facial expression, based at least on a second image previously captured, the first facial expression and the second facial expression being of a same first type of facial expression;

determining at least one difference between the at least one characteristic of the first facial expression determined and the at least one characteristic of the second facial expression determined; and generating an output signal indicating a condition of the person based at least on the at least one difference determined, wherein at least one of previously capturing of the first image and previously capturing of the second image includes previously capturing a video of at least the mouth of the person and determining a characterizing frame of the video acquired as at least one of the first image acquired and the second image acquired, and wherein one of
- the characterizing frame of the video acquired is automatically determined based on a criterion, or
- a user or the person is prompted to select one of the frames of the video acquired as the characterizing frame.

22. The non-transitory computer-readable data storage medium of claim 21, wherein the criterion is that the characterizing frame is a frame in which at least one of the at least one characteristic of the first facial expression and at least one characteristic of the second facial expression has an extremum, an average or a median within the video acquired.

23. The non-transitory computer-readable data storage medium of claim 21, wherein a third characteristic of the at least one characteristic of the first facial expression and the at least one characteristic of the second facial expression is a time from a starting frame of the video acquired, to the frame determined as the respective first image or second image.

* * * * *